United States Patent
Ashu et al.

(10) Patent No.: US 12,200,408 B1
(45) Date of Patent: Jan. 14, 2025

(54) BADGE WITH INTEGRAL CAMERA

(71) Applicants: Wilson Ekanyie Ashu, Fort Worth, TX (US); Laura Ngwisang, Fort Worth, TX (US); Vanessa Shabu Fahdeen, Plano, TX (US)

(72) Inventors: Wilson Ekanyie Ashu, Fort Worth, TX (US); Laura Ngwisang, Fort Worth, TX (US); Vanessa Shabu Fahdeen, Plano, TX (US)

( * ) Notice: Subject to any disclaimer, the term of this patent is extended or adjusted under 35 U.S.C. 154(b) by 1254 days.

(21) Appl. No.: 15/938,179

(22) Filed: Mar. 28, 2018

(51) Int. Cl.
*H04N 23/62* (2023.01)
*A44C 3/00* (2006.01)
*H04B 1/034* (2006.01)
*H04N 7/18* (2006.01)
*H04N 23/56* (2023.01)
*A61N 1/16* (2006.01)

(52) U.S. Cl.
CPC ............ *H04N 7/185* (2013.01); *A44C 3/001* (2013.01); *H04B 1/0343* (2013.01); *H04N 7/188* (2013.01); *H04N 23/56* (2023.01); *H04N 23/62* (2023.01); *A61N 1/16* (2013.01)

(58) Field of Classification Search
CPC .... H04N 7/185; H04N 5/23216; H04N 23/62; A44C 3/001; A61N 1/16; H04B 1/0343
See application file for complete search history.

(56) References Cited

U.S. PATENT DOCUMENTS

| | | | |
|---|---|---|---|
| 2004/0085203 A1* | 5/2004 | Junqua | G07B 15/00 340/539.11 |
| 2016/0182850 A1* | 6/2016 | Thompson | H04N 1/00106 348/158 |
| 2017/0230605 A1* | 8/2017 | Han | H04N 7/185 |
| 2018/0359374 A1* | 12/2018 | Latheef | G06F 3/0488 |

* cited by examiner

*Primary Examiner* — Dave Czekaj
*Assistant Examiner* — Berteau Joisil
(74) *Attorney, Agent, or Firm* — Kenneth L. Tolar

(57) ABSTRACT

A badge formed of a planar sheet includes a front surface, a rear surface and a central opening. A camera module is attached to the rear surface and includes a camera lens and control panel positioned within the central opening. The camera is activated either manually using the control panel or automatically by one or more atmospheric sensors. The badge further includes a wireless-telephone transmitter for automatically transmitting the images to a remote electronic device to assist others with properly assessing and investigating an ongoing crime or emergency event.

7 Claims, 2 Drawing Sheets

BADGE WITH INTEGRAL CAMERA

CROSS REFERENCE TO RELATED APPLICATIONS

None.

BACKGROUND OF THE INVENTION

The present invention relates to a badge having an integral camera that allows a policeman or other wearer to conveniently record and transmit images of a surrounding area without wearing a burdensome body camera.

DESCRIPTION OF THE PRIOR ART

In light of widespread complaints of police brutality, policemen in many jurisdictions are required to wear body cameras in order to document events surrounding police interactions with civilians. Moreover, body cameras can also assist a policeman with recording valuable video evidence for later use in criminal investigations. However, because of the weight and discomfort associated with conventional body cameras and the threat of self-incrimination, policemen often stow an assigned body camera, where it is useless for recording emergency events or conducting surveillance.

In addition, body cameras are typically not designed to record images for immediate retrieval and usually require the user to manually activate the device. If the camera is disabled or stowed and an emergency event suddenly occurs, video of the surrounding area will not be recorded. However, recording images immediately prior to or during such an event could be a valuable tool for law enforcement to facilitate a proactive intervention or to identify a perpetrator. A conventional body camera however includes no means for automatically capturing images during a potential emergency event.

Accordingly, there is currently a need for a body camera that is less burdensome and obstructive than conventional body cameras and which automatically records images in certain potentially dangerous situations. The present invention addresses this need by providing a badge having an incorporated camera that allows a policeman to more easily and comfortably record surrounding images. The badge includes one or more atmospheric sensors that automatically activate the camera upon detection of potentially dangerous environmental hazards. Furthermore, the badge includes a wireless-telephone transmitter that automatically sends recorded images to a remote electronic device to assist backup responders or supervisors with properly assessing and responding to the emergency event, or with investigating the event afterward.

SUMMARY OF THE INVENTION

The present invention relates to a badge with an integral camera including a substantially planar sheet having a front surface, a rear surface and a central opening. On the front surface is identifying indicia that associates the badge wearer with a particular organization, such as a police department, a security company or similar group of responders. The rear surface includes a fastener for securing the sheet to a wearer's clothing, belt or similar article as with a conventional badge. The sheet further includes a camera module having a digital camera, a touch-screen display and an LED on a front surface that are all positioned within the central opening. Using the display, a wearer can capture still or video images of a surrounding area and wirelessly transmit them to a remote electronic device. The recorded images can, therefore, be transmitted to dispatchers, backup officers and other personnel to facilitate an appropriate response to a crime scene or other emergency event.

It is therefore an object of the present invention to provide a badge having an integral camera.

It is therefore another object of the present invention to provide a badge that can record and wirelessly transmit images of a surrounding area to assist remote recipients with properly responding to or investigating an emergency event.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
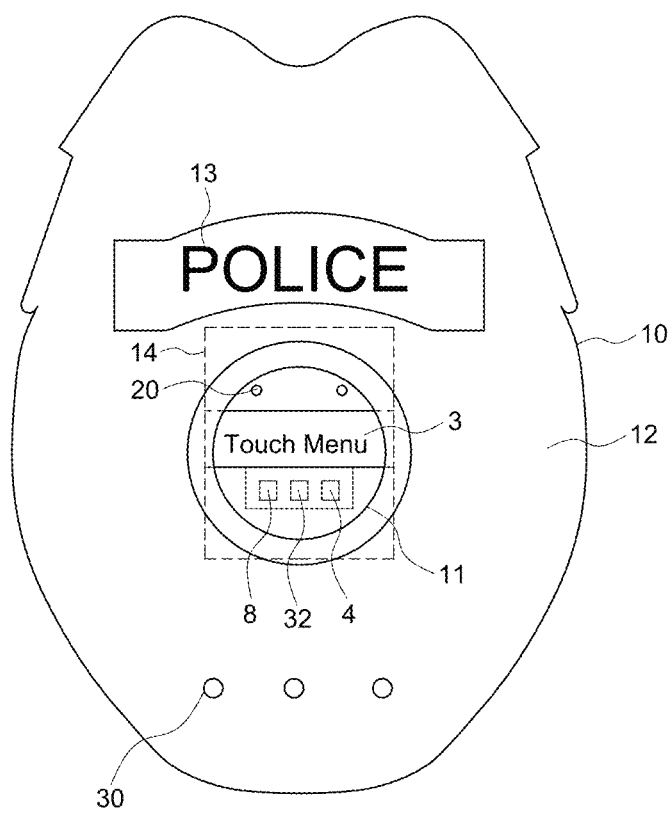
FIG. 1 is a front, plan view of the badge according to present invention.
Figure 2:
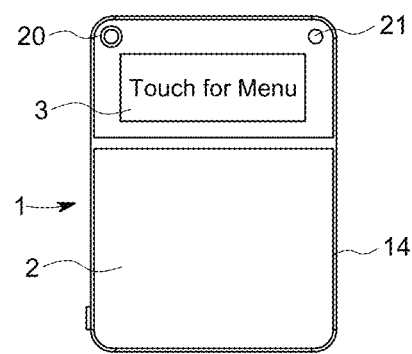
FIG. 2 is an isolated view of the camera module.
Figure 3:
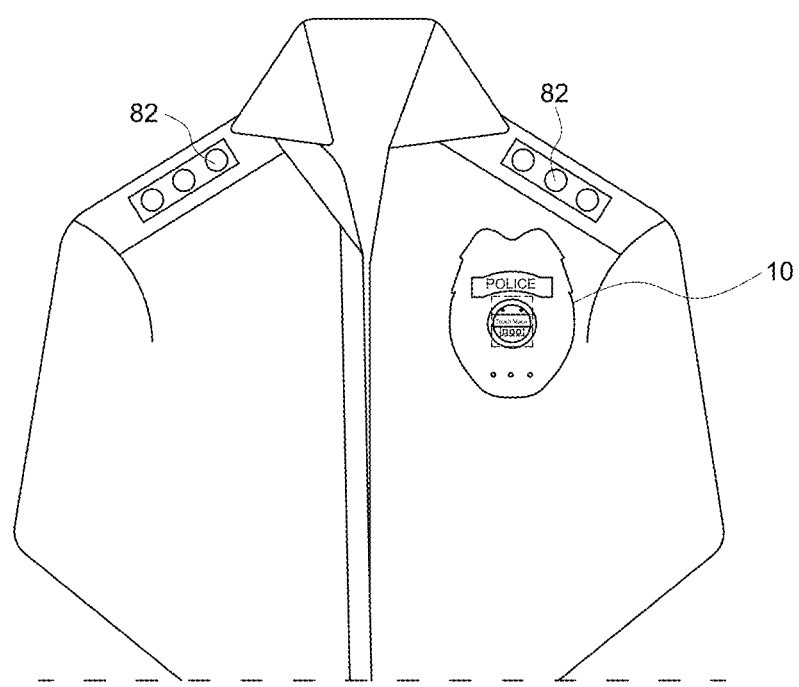
FIG. 3 depicts an alternate embodiment of the present invention.

The present invention relates to a badge with an integral body camera including a substantially planar or low-profile sheet 10 having a front surface 12, a rear surface and a central opening 11. The sheet may have an outline similar to a conventional policeman's badge, or any other desired configuration that corresponds to a wearer's official capacity. On the front surface is identifying indicia 13 that associates the badge wearer with a particular organization, such as a police department, a security company or similar response or enforcement group.

Attached to the rear surface of the sheet is a camera module 14 comprising a housing 1 having a front surface 2, a rear surface, a plurality of peripheral walls, and an interior chamber. On the front surface is a touch-screen display 3 in communication with a wireless-telephone transmitter 32, and a microprocessor 4 with an associated operating system for programming and controlling all of the various electronic devices described herein. The processor and wireless-telephone transmitter are mounted on a printed circuit board 8 within the interior chamber. The rear surface of the sheet includes a layer that protects the wearer from exposure to any radiation emanating from the telephone transmitter and a fastener for securing the badge to a wearer's clothing, belt or similar article.

Adjacent to the display 3 is a digital camera 20 in communication with the wireless-telephone transmitter and microprocessor for recording and wirelessly transmitting images of a surrounding area to a designated remote electronic device carried by a supervisor, a dispatcher or backup responders. An adjacent LED 21 illuminates the surrounding area for the camera if needed and also projects light beams for ambient attenuation determinations.

The touch-screen display 3, LED 21 and camera 20 are positioned within the central opening 11 so as to be easily accessible by the badge wearer. Using the display, a wearer can instruct the camera to capture either still or video images of a surrounding area and to transmit them to the designated remote electronic device to assist dispatchers or other responders with properly assessing an ongoing crime or emergency event.

Proximal the lower end of the sheet is one or more sensors 30 for detecting noxious liquid or gaseous substances that could indicate the presence of explosives, airborne contaminants, such as smoke or pollutants, poison gas, and other potentially harmful or dangerous environmental substances. The sensors could include but are not limited to motion sensors, passive infrared (PIR), microwave, dual-technology motion, area reflective, ultrasonic, vibratory, and intercom/hub.

Accordingly, a policeman or other wearer can easily transmit still or video images to a remote dispatcher, supervisor, or perhaps a backup responder to immediately assess a potential disaster, emergency or crime scene. The transmitted images will assist the recipient with preparing an appropriate response or with investigating the event at a later time. If any of the sensors detect an unusual condition, the camera is automatically activated and any recorded images are transmitted via the wireless-telephone transmitter to a remote device to allow a recipient to immediately implement appropriate responsive action.

The above-described device is not limited to the exact details of construction and enumeration of parts provided herein. For example, the device is not limited to the sensors described above and could also include metal detectors for identifying weapons, or other sensors for detecting dangerous non-metallic objects, such as powderous explosives or plastic, as with airport detectors. The camera could be programmed to capture images of the individuals carrying detected weapons or powder for later review and retrieval. The system could also be in an airplane to record events during a given flight to assist with preventing or investigating certain occurrences, such as a hijacking. In addition, the system could communicate with a long-distance motion sensor for receiving and relaying images of activity occurring at remote locations. Finally, instead of or in addition to being incorporated into a badge, the camera and other electronic components could be incorporated into shoulder buttons 82 on a uniform shirt, eyeglasses or other clothing items which can operate independently of or in cooperation with the badge camera system described herein. Furthermore, the size, shape and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A badge with integral body camera comprising:
   a sheet having a front surface, a rear surface and a central opening;
   means for attaching said sheet to a clothing item;
   a camera attached to said sheet for capturing images of a surrounding area;
   means for wirelessly transmitting the images to a remote electronic device wherein said means comprises a wireless-telephone transmitter in communication with said camera, whereby a wearer can capture either still and video images of a surrounding area and transmit the still and video images to the remote electronic device to assist others with properly assessing and investigating an ongoing crime or emergency event;
   means for automatically activating said camera;
   a touch-screen display received within said central opening and in communication with said wireless-telephone transmitter and said camera for manually capturing images of a surrounding area and for manually transmitting the images to the remote electronic device.

2. The badge with integral body camera according to claim 1 wherein said means for automatically activating said camera and for wirelessly transmitting the images to a remote electronic device comprises an atmospheric sensor in communication with said camera and said wireless-telephone transmitter that activates said camera and wireless-telephone transmitter upon detecting an atmospheric hazard.

3. The badge with integral body camera according to claim 1 further comprising identifying indicia on the front surface of said sheet that associates a badge wearer with a discrete organization.

4. The badge with integral body camera according to claim 1 wherein the rear surface of said sheet includes a protective layer that protects the wearer from exposure to any radiation emanating from the wireless-telephone transmitter.

5. The badge with integral body camera according to claim 1 further comprising an LED positioned within the central opening for illuminating the surrounding area for the camera.

6. A badge with integral body camera comprising:
   a sheet having a front surface, a rear surface and a central opening;
   means for attaching said sheet to a clothing item;
   a camera attached to said sheet for capturing images of a surrounding area;
   means for wirelessly transmitting the images to a remote electronic device wherein said means comprises a wireless-telephone transmitter in communication with said camera, whereby a wearer can capture either still and video images of a surrounding area and transmit the still and video images to the remote electronic device to assist others with properly assessing and investigating an ongoing crime or emergency event;
   means for automatically activating said camera;
   a protective layer on the rear surface of said sheet that protects the wearer from exposure to any radiation emanating from the wireless-telephone transmitter.

7. A badge with integral body camera comprising:
   a sheet having a front surface, a rear surface and an opening;
   means for attaching said sheet to a clothing item;
   a camera attached to said sheet for capturing images of a surrounding area;
   means for wirelessly transmitting the images to a remote electronic device wherein said means comprises a wireless-telephone transmitter in communication with said camera, whereby a wearer can capture either still and video images of a surrounding area and transmit the still and video images to the remote electronic device to assist others with properly assessing and investigating an ongoing crime or emergency event;
   means for automatically activating said camera;
   an LED positioned within the central opening for illuminating the surrounding area for the camera.

* * * * *